US00PP16980P2

(12) United States Plant Patent
Schoenmakers

(10) Patent No.: US PP16,980 P2
(45) Date of Patent: Aug. 8, 2006

(54) ***FITTONIA* PLANT NAMED 'JOLY JOSAN'**

(50) Latin Name: *Fittonia verschaffeltii*
Varietal Denomination: Joly Josan

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 19 days.

(21) Appl. No.: 11/166,653

(22) Filed: Jun. 25, 2005

(51) Int. Cl.
*A01H 5/00* (2006.01)

(52) U.S. Cl. ..... Plt./373

(58) Field of Classification Search ..... Plt./373
See application file for complete search history.

(56) References Cited

PUBLICATIONS http://www.cpvo.eu.int/module_tech/rights_granted-.php?SPECIED=FIT02.*

* cited by examiner

*Primary Examiner*—Kent Bell
*Assistant Examiner*—W. C. Haas
(74) *Attorney, Agent, or Firm*—Mark P. Bourgeois

(57) ABSTRACT

A new cultivar of *Fittonia* plant named 'Joly Josan' that is characterized by green leaves with red veins and a compact habit.

1 Drawing Sheet

Botanical classification: *Fittonia verschaffeltii.*
Variety denomination: 'Joly Josan'.

BACKGROUND OF THE INVENTION

The present invention relates to a new and distinct cultivar of *Fittonia* plant botanically known as *Fittonia verschaffeltii* and hereinafter referred to by the cultivar name 'Joly Josan'.

The new cultivar was discovered by the inventor in a cultivated area of Haaren, The Netherlands in 2002. 'Joly Josan' was discovered as a naturally occurring whole plant mutation of *Fittonia verschaffeltii* 'Josan' (not patented).

Asexual reproduction by terminal cuttings of the new cultivar 'Joly Josan' was first done in 2002 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Joly Josan'.

1. *Fittonia* 'Joly Josan' exhibits green leaves with red veins.
2. *Fittonia* 'Joly Josan' exhibits a compact habit.

The closest comparison cultivar is the parent *Fittonia* 'Josan'. The new cultivar 'Joly Josan' is distinguishable from 'Josan' by the following characteristics:

1. 'Joly Josan' has a more compact habit than 'Josan'.
2. 'Joly Josan' has leaf margins that are less wavy than 'Josan'.
3. 'Joly Josan' has leaf veins that are redder than those of 'Josan'.

BRIEF DESCRIPTION OF THE DRAWING

The accompanying photograph illustrates the distinguishing traits of *Fittonia* 'Joly Josan'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Joly Josan'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Joly Josan' has not been tested under all possible conditions and phenotypic differences may be observed with variations in environmental, climatic, and cultural conditions, however, without any variance in genotype.

Botanical classification: *Fittonia verschaffeltii* 'Joly Josan'.
Use: Ornamental.
Parentage: 'Joly Josan' is a naturally occurring whole plant mutation of *Fittonia* 'Josan'.
Vigor: Moderate.
Growth rate: Moderate.
Growth habit: Broad spreading, upright.
Plant shape: Flattened globuse.
Suitable container size: 8.5 cm. diameter container.
Height: Average 5.5 cm.
Width: Average 8.8 cm.

Hardiness: USDA Zone 10.
Propagation: Terminal cuttings.
Time to initiate roots: Approximately 21 days to produce roots on an initial cutting at 24 degrees Centigrade.
Time to produce a rooted cutting: Approximately 35 days to produce a rooted cutting at 24 degrees Centigrade.
Crop time: 12 weeks.
Root system: Fine and fibrous.
Stem:
*Branching habit.*—Freely branching.
*Average number of lateral branches.*—4.
*Pinching.*—No.
*Lateral branch diameter.*—2 mm. in diameter.
*Lateral branch length.*—2.7 cm. in length.
*Lateral branch strength.*—Moderately strong.
*Stem color.*—200C with internodes 144B.
*Pubescence.*—Dense, length 1.5 mm., color N155A.
*Internode length.*—1.7 cm. between nodes.
*Shape.*—Rounded, dull.
*Surface.*—Dull.
*Stem strength.*—Moderate.
Foliage:
*Leaf arrangement.*—Opposite.
*Compound or single.*—Single.
*Leaf shape.*—Elliptical, slightly curved.
*Leaf apex.*—Rounded.
*Leaf base.*—Attenuate.
*Leaf texture.*—Glabrous, slightly rugose, prominent venation.
*Leaf length.*—Average 4.1 cm. in length.
*Leaf width.*—2.4 mm. in width.
*Quantity of leaves per lateral branch.*—Average 4.
*Pubescence.*—Short hairs on margins, undersides, and secondary veins, 0.5 mm. in length, N155A.
*Leaf margin.*—Entire to repand.
*Vein pattern.*—Pinnate.
*Young leaf color,* (*upper surface*).—143A, darker towards margin.
*Young leaf color,* (*lower surface*).—143A.
*Mature leaf color,* (*upper surface*).—139A.
*Mature leaf color,* (*lower surface*).—138A to 138B.
*Vein color* (*upper surface*).—47A, leaf margins darker 46A to 46B.
*Vein color* (*lower surface*).—145A, leaf margins 53A.
*Leaf attachment.*—Petiolate.
*Petiolate dimensions.*—Average 6 mm. in length, 2 mm. in diameter, 1.5 mm. in height.
*Petiole color.*—Upper surface 47A, lower surface 146C, striped 184A to 184B.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'Joly Josan' as described and illustrated.

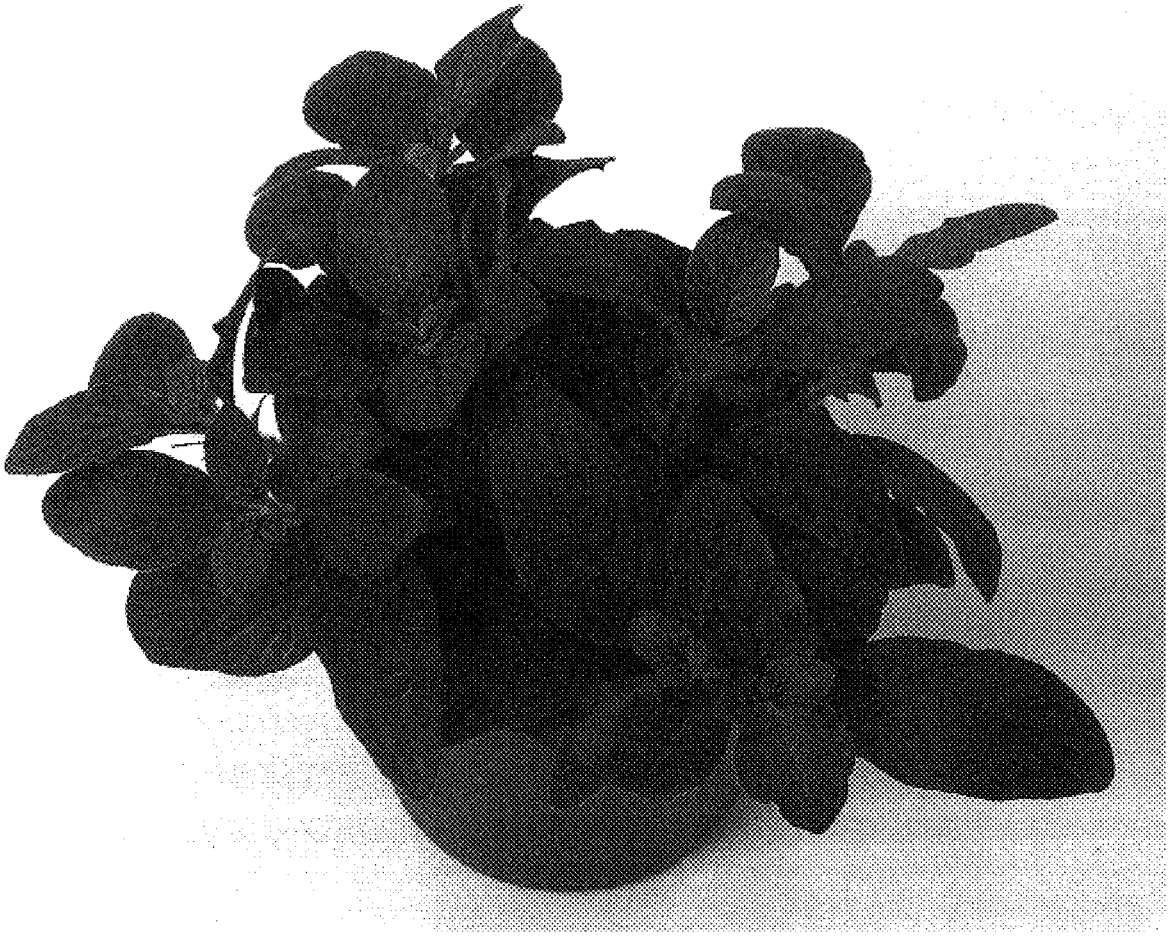

* * * * *